United States Patent [19]

Sachse et al.

[11] Patent Number: 4,950,278
[45] Date of Patent: Aug. 21, 1990

[54] ENDOSCOPE FOR REMOVAL OF TISSUE

[76] Inventors: Hans E. Sachse, Lerchenstrasse 55, 8500 Nuremberg 90, Fed. Rep. of Germany; Rainer Sachse, 720 NE. 72 Ter., Miami, Fla. 33138

[21] Appl. No.: 401,505

[22] Filed: Aug. 30, 1989

Related U.S. Application Data

[63] Continuation of Ser. No. 82,239, Aug. 6, 1987, abandoned, which is a continuation-in-part of Ser. No. 829,103, Feb. 14, 1986, Pat. No. 4,756,309.

[30] Foreign Application Priority Data

Aug. 6, 1986 [DE] Fed. Rep. of Germany ....... 3626684

[51] Int. Cl.$^5$ ............................................. A61F 17/32
[52] U.S. Cl. ......................................... 606/170; 128/6
[58] Field of Search ........................ 604/22; 128/6–7, 128/303 R, 305; 606/170, 171, 167

[56] References Cited

U.S. PATENT DOCUMENTS

| | | | |
|---|---|---|---|
| 2,708,437 | 5/1955 | Hutchins | 128/7 |
| 3,835,858 | 9/1974 | Hogen | 128/305 |
| 3,847,154 | 11/1974 | Nordin | 128/305 |
| 3,937,222 | 2/1976 | Banko | 128/305 |
| 4,137,920 | 2/1979 | Bonnet | 128/7 |
| 4,455,509 | 5/1989 | Auth | 128/305 |
| 4,461,305 | 7/1984 | Cibley | 128/305 |
| 4,499,899 | 2/1985 | Lyons, III | 128/305 |
| 4,539,976 | 9/1985 | Sharpe | 128/6 |
| 4,756,309 | 6/1988 | Sachse et al. | 128/305 |

Primary Examiner—Steven C. Pellegrino
Assistant Examiner—Kathleen A. Daley
Attorney, Agent, or Firm—Keil & Weinkauf

[57] ABSTRACT

An endoscope which contains, in a housing, in parallel relationship, a light guide, at least one flushing duct, and a continuously driven shaft which carries at its end, protruding in operation from the tip of the endoscope, a cutting instrument having a plurality of cutting blades. This design makes it possible to remove pieces of tissue, for example, for laboratory tests in a more intact way than was possible with the endoscope according to the parent U.S. Pat. No. 4,756,309. The endoscope disclosed herein lends itself to a wide variety of medical fields.

21 Claims, 8 Drawing Sheets

ENDOSCOPE FOR REMOVAL OF TISSUE

This application is a continuation of application Ser. No. 07/082,239, filed on Aug. 6, 1987 now abandoned. Which is a continuation-in-part of U.S. Ser. No. 829,103, now U.S. Pat. No. 4,756,309 issued July 12, 1986.

The parent U.S. patent is based on an endoscope consisting of a tube-shaped shaft, of a lens system with a light guide located in the tube of the endoscope, the viewing aperture of said lens system and light guide being located as an extension of the tube axis, or diagonally to the tube axis, or being arranged offset and in parallel to the tube axis, and consisting of one or several flushing ducts. In this case, a rotating instrument is provided at the endoscope tube that removes or breaks up tissue, etc. With respect to other developments of this endoscope, reference is made to the disclosure content of the parent Patent Application No. P 36 01 453.2, that is hereby made into the content of the disclosure of the present application.

The endoscope according to the parent patent has basically had good results. It is the objective of the present invention to expand or improve the possibilities of application and the developments of the endoscope according to the main patent.

The invention may be employed in all fields in which direct visual control by the operating surgeon is not possible and therefore the viewing aid of the endoscope must be used, and in which at the same time a removal of tissue, a breaking-up of pieces, etc. by means of a rotating instrument is advantageous or even necessary. In the urological field, for example, this would apply to the grinding-away of stones (gallstones, kidney stones or the like). Also the removal of scar tissue in different branches of surgery as well as the removal and breaking-up of foreign bodies that have entered the human body or hollow organs of the human body can be carried out well endoscopically according to the invention.

With the abovementioned object in mind the invention consists, briefly, in an endoscope having a front or tip end and a rear end, and comprising a tubular housing, a lense system with a light guide extending longitudinally in said housing and having its viewing aperture at the rear end of the endoscope, a continuously driven shaft also extending longitudinally in said housing in parallel relationship to said light guide and comprising at its front end, protruding in operation from the tip of the endoscope a rotating working head, and at least one flushing duct and means for introducing flushing liquid into said flushing duct, wherein said working head is a cutting instrument having a plurality of cutting blades having cutting edges. In this manner, tissue pieces, for example, for testing as to whether a carcinoma is present or the like, can be removed in a more intact way than in the case of a removal of tissue by means of a grinding or milling instrument which practically completely crushes the tissue and makes the microscopic examination more difficult or impossible.

Preferably the rotating working head is in the form of a tube which is closed at one end and which has a wavy cutting edge, that is a cutting edge of undulating shape. As a result, tissue pieces may also be cut off if this seems more advantageous operatively. In a targeted way, very small, superficial tissue pieces can be removed.

It is, furthermore, advantageous if the endoscope also comprises a tubular element of a diameter only slightly larger than that of the rotating working head and if the tubular element and the working head are arranged for longitudinal movement relatively to each other. Preferably the tubular element, in turn, is pot-shaped and forms with the working head a hollow space for the collection of removed tissue. This hollow space than acts as a type of collecting receptacle in which the cut-off tissue is collected and is therefore available for later testing (a so-called biopsy). In another embodiment of the invention the rotating working head is in the form of a truncated cone and has a cutting edge. This embodiment also has blades and is therefore used for the cutting off of larger tissue pieces.

Another advantageous development of the endoscope according to the invention resides in that the endoscope also comprises a turbine for driving the shaft of the working head. It results in an elastic drive of the instrument. In a preferred embodiment of the invention, the drive takes place by means of the flushing liquid that is present anyway and must be set in motion, whereby therefore a separate drive of the instrument is not required.

As a consequence, a flushing can be achieved that takes place continuously and continuously carries away the turbid liquid that occurs in the treatment area as a result of the instrument, so that the operating surgeon always has a good view and can therefore continue to work without interruption. Otherwise, it would be necessary for the operating surgeon to interrupt the work, take out the endoscope, rinse out the treated area and continue the work after the endoscope was inserted again. The resulting loss of time or the prolonging of the operating time as well as the repeated inserting and removing of the endoscope are avoided by means of the invention. Or it is avoided that, by means of the insertion of a small tube, an additional discharge possibility must be created from the operating site to the outside.

By the provision of an electrically heatable milling, cutting or grinding head, the tissue to be treated or removed is heated and therefore denatured so that it can be removed better by means of the instrument than soft tissue that, in contrast, was left in its normal condition. Since, as a result of the effect of the heat, the veins and arteries are closed, bleeding is also avoided that otherwise is caused by the removal.

Other advantages and characteristics of the invention are found in the following description and the pertaining drawing of embodiments according to the invention. In the drawings, that have the same reference numbers for parts that are the same as in the parent patent.

Figure 1:
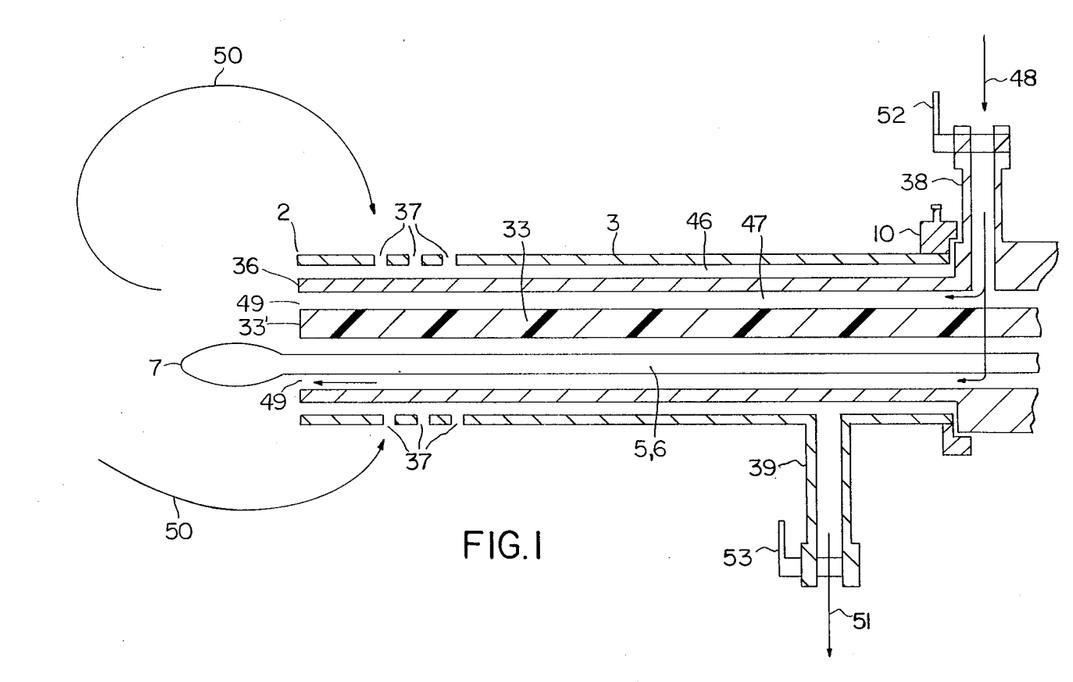
FIG. 1 is a longitudinal sectional view of the endoscope tube with the pertaining parts and of an embodiment of the flushing operation according to the invention.

In FIG. 1, reference number 2 generally shows the tip of the endoscope at which, toward the right, the endoscope tube is connected. In addition, driving and actuating means are also provided which in FIG. 1 are on the right of the endoscope tube and are shown diagrammatically in the embodiment of FIGS. 9 and 10. In addition, reference is made to the parent U.S. Pat. No. 4,756,309.

The outer tube 3 of the endoscope surrounds a first ring-cylindrical flushing duct 46 that, on the inside, is delimited by an inner tube 36, on the inside of which the lens system and the cold light guide 33 as well as instrument 7 carrying the shaft 5 with the bearing 6 are located. The above-mentioned parts 33 as well as 5, 6 are surrounded by another, inner, ring-cylindrical flushing duct 47. The continuous flushing in this embodiment takes place as follows:

The clean flushing liquid is according to the Arrow 48, through an inlet connection piece 38, fed into the inner ring-cylindrical flushing duct 47 and emerges at its front end according to Arrows 49. The flushing liquid therefore reaches the operating area of the instrument 7 and by means of the corresponding suction, at a hollow connection piece 39, according to the Arrow 50, is guided into passage openings 37 into the front area of the outer tube of the endoscope and through the outer ring-cylindrical flushing duct 46. From here, the discharge takes place according to reference number 51 via the outlet connection piece 39.

Figure 2:
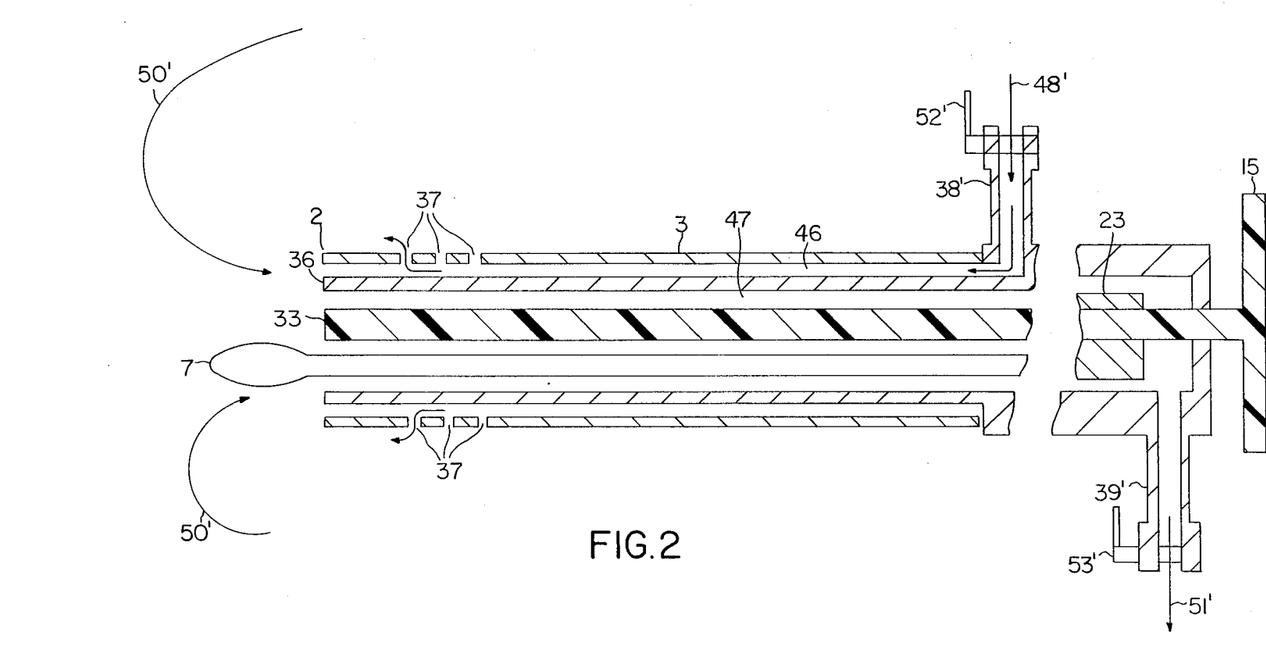
FIG. 2 is also a longitudinal sectional view of another embodiment of the endoscope tube with a flushing operation according to the invention.

In the embodiment of FIG. 2, the constructional arrangement is modified to the extent that the inlet connection piece 38' guides the flushing liquid 48' into the outer ring-cylindrical flushing duct 46, from which this clean flushing liquid is sucked off via the oppenings 37 in the outer tube 3 of the endoscope, according to the Arrows 50', toward the operating area of the instrument 7 and from there, via the inner ring-cylindrical flushing duct 47 and the outlet connection piece 39' according to reference number 51'.

In both embodiments, the operating area of the instrument 7 is constantly supplied with clean flushing liquid and the turbid liquid that occurs there and is mixed with tissue parts, stone particles, blood, etc. is also continuously sucked off.

For the control of the inflow and outflow of the flushing liquid, a control means 52, 52' may be provided at the respective inlet connection piece and a control means 53 and 53' may be provided at the respective outlet connection piece. Naturally, instead of the control means indicated in this embodiment, differently developed throttling devices for the flushing current may also be provided.

Figure 3:
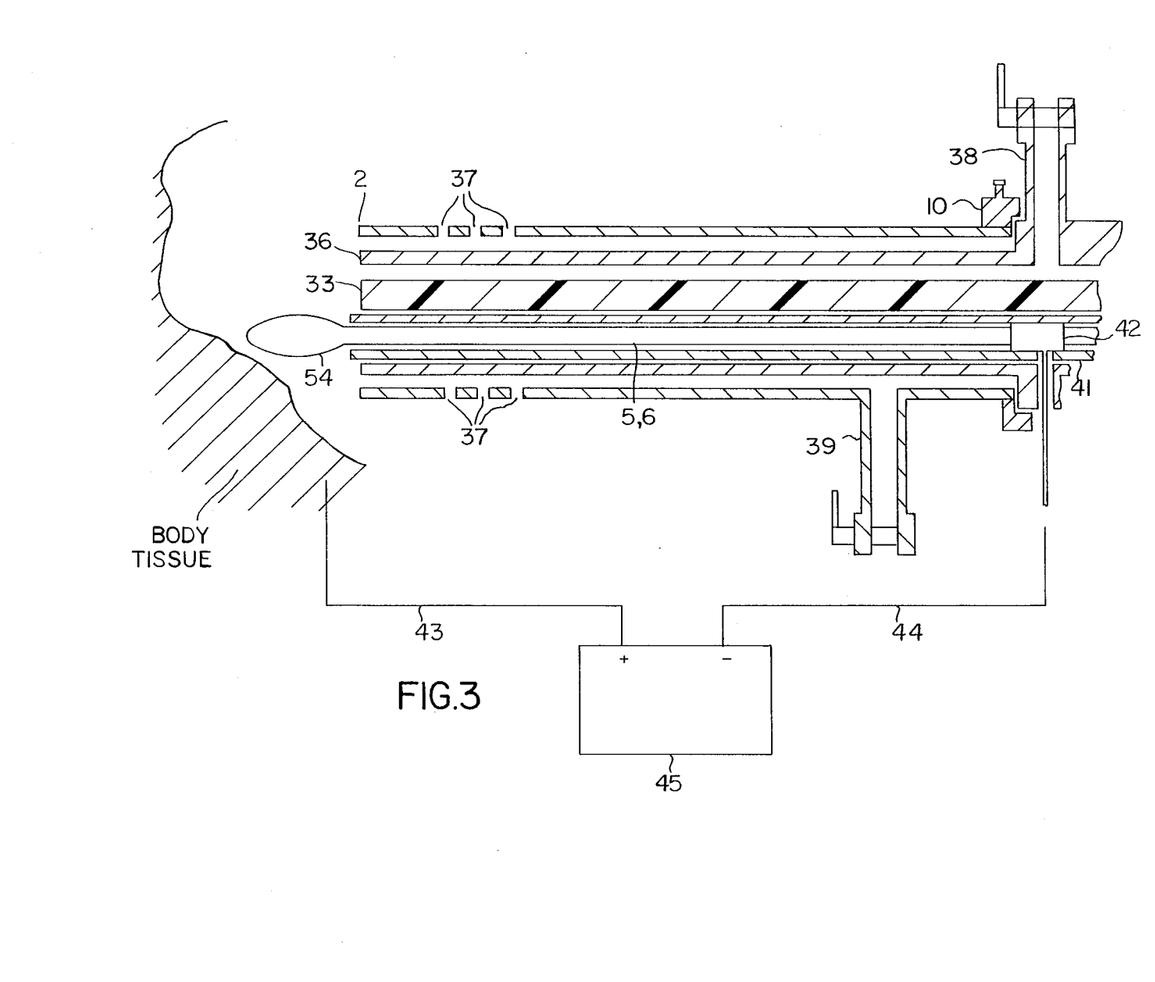
FIG. 3 is also a longitudinal sectional view of an endoscope tube with an electrical heating of the instrument.

The instrument 7 may be grinding or milling head that can be screwed off (see parent U.S. Pat. No. 4,756,309). In the embodiment according to FIG. 3, the instrument that in this case has the number 54, can be heated electrically. For this purpose, from a current source 45 that is shown in diagram form, one pole according to Number 43 can be guided to the patient's body, and the other pole, according to Number 44, can be guided to a connection 42 and from there, via the shaft 5, 6, to the actual instrument 54. 41 is an insulation. The metallic grinding head may, on the other hand, be heated by means of suitable electrical energy (such as waves) supplied from the outside, in which case, however, the endoscope and the shaft handle 5 must consist of a material (such as plastic) that is not heated by this electric energy.

Figure 4:
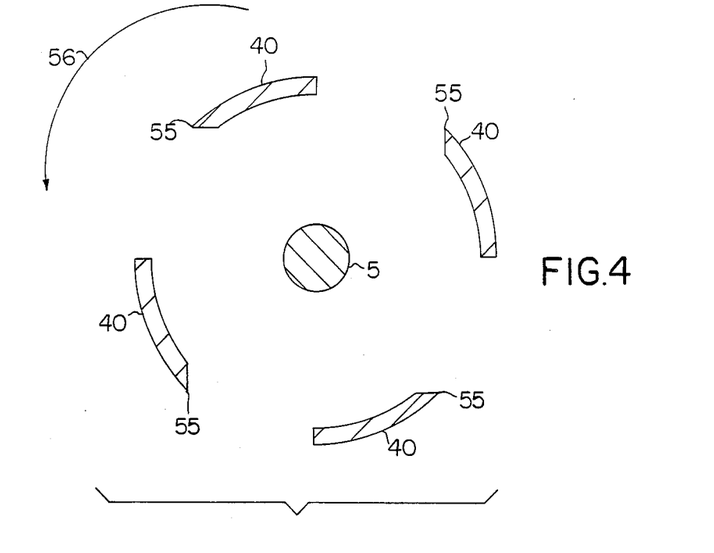
FIG. 4 is a cross-sectional view according to the Line IV—IV in FIG. 5 of the embodiment of a cutting instrument.
Figure 5:
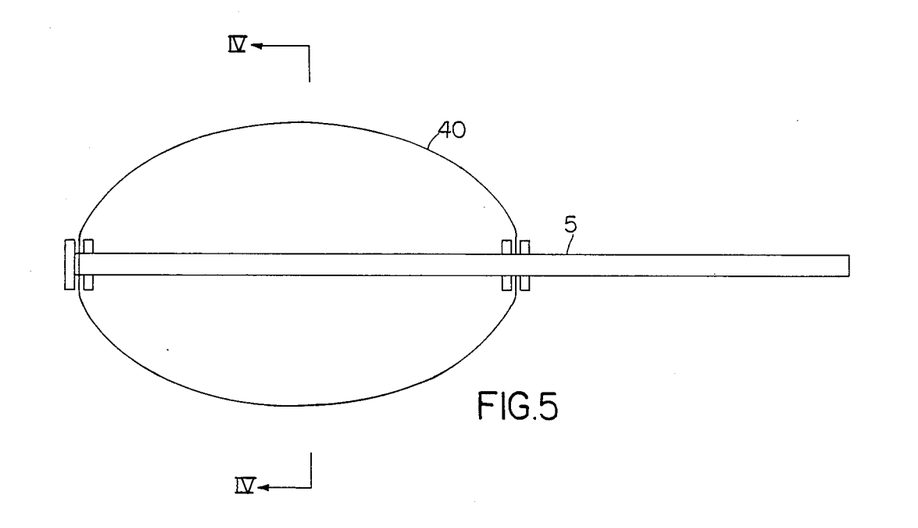
FIG. 5 is a lateral view of the cutting instrument according to the sectional view of FIG. 4.

FIGS. 4 and 5 show another development of the rotating instrument used here. Distributed on a circular ring, approximately crescemt-shaped cutting blades 40 are provided that each have a cutting edge 55 that is aimed into the rotating direction. The cutting blades are arranged approximately on a spherical surface. Their rotating direction has the number 56. The crescent-shaped blades may also extend diagonally so that they are located at a certain angle with respect to the axis and then cut into the tissue correspondingly diagonally.

Figure 6:
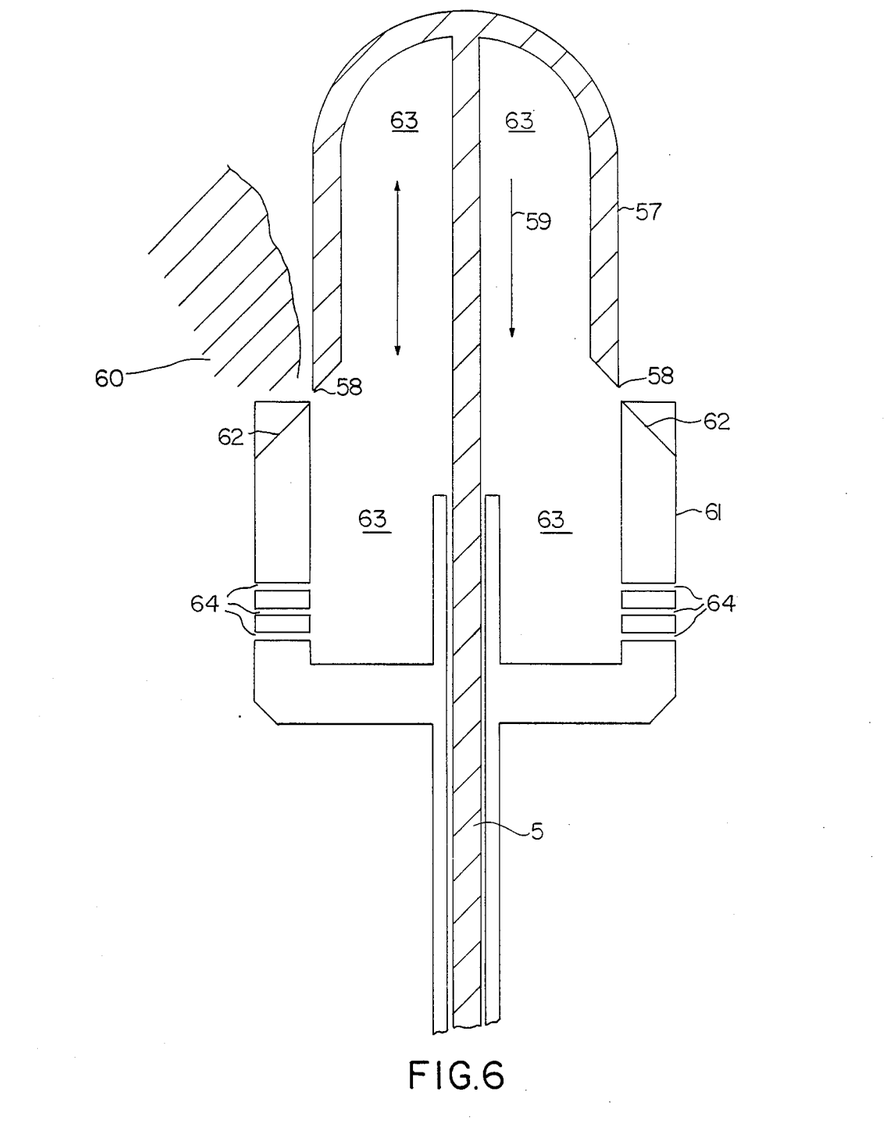
FIG. 6 is a longitudinal sectional view of another embodiment of a cutting instrument.

The embodiment according to FIG. 6 shows a rotating instrument 57 that may have the shape of a tube, is closed at one front side and at the other front side, has cutting edges 58 that rotate along with it. These cutting edges may be smooth or wavy. This instrument is firmly or connectably connected with the drive shaft 5. Its cutting edges 58 are preferably, according to this embodiment, directed toward the endoscope, i.e., approximately in the direction of the drive shaft, so that, when the instrument is pulled in the direction 59 of the arrow, it can come into cutting contact with the respective tissue that, in this case, has the number 60. This cutting instrument may be used by itself or, in a preferred embodiment of the invention, together with an approximately pot-shaped tubular element 61, the upper edges of which, as shown by number 62, may also be cut off or chamfered. In this case, the cutting instrument 57 and the tubular element 61 form a hollow space 63 that is approximately closed, in which tissue pieces are collected that were cut off by the cutting instrument, so that they later, after the endoscope was taken out, will be available for tests of the like. Before the start of the operation, the cutting instrument 57 is moved out against the direction of the Arrow 59. In the wall of the tubular element 61, breakthroughs 64 are provided for the discharge of the liquid that collects there. Naturally, the cutting instrument 57 is not limited to the shown cylindrical shape. It is important in this embodiment that it is closed on one side (on top in FIG. 6) and has approximately the shape of a tube.

Another cutting instrument according to the invention is a tube that is open on both sides and at one edge (front surface) or at both edges (front surfaces) is developed as a cutting edge with a smooth or wavy course. This embodiment is not shown in the drawing.

Figure 7:
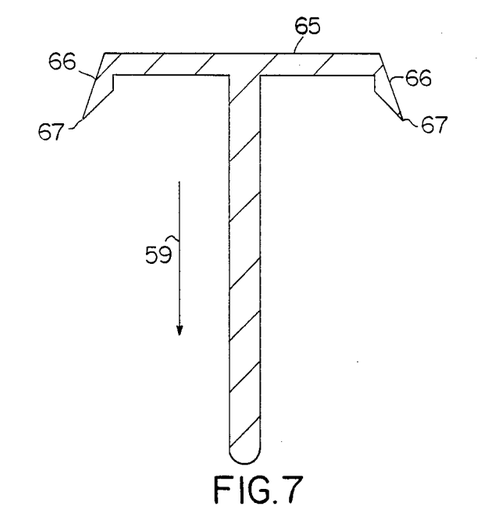
FIG. 7 is a longitudinal sectional view of another embodiment of a cutting instrument.
Figure 7A:
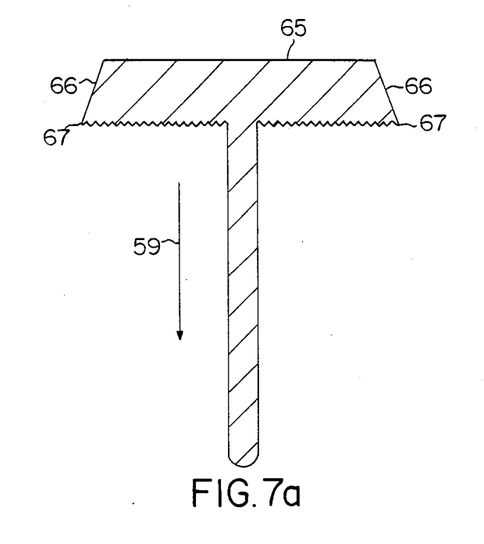
Figure 8:
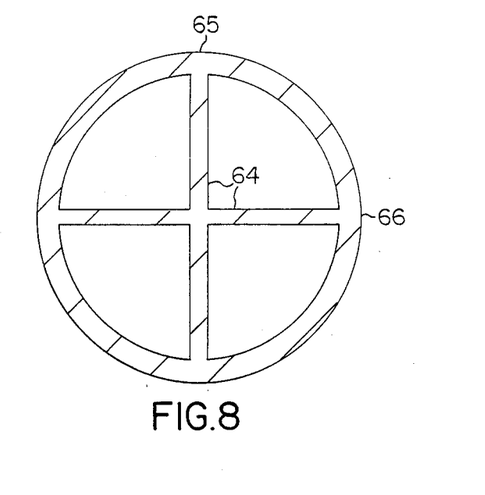
FIG. 8 is a top view of FIG. 7.

The cutting instrument according to the embodiment shown in FIGS. 7 and 8 has, at the end of shaft 5, a spider 64,65 that carries a truncated cone-shaped section 66 that ends in a cutting edge 67 having a smooth or wavy configuration, an example for the latter being separately shown in FIG. 7a. For the purpose of operating, it is moved in the direction of the Arrow 59 or is moved out against this direction.

Figure 9:
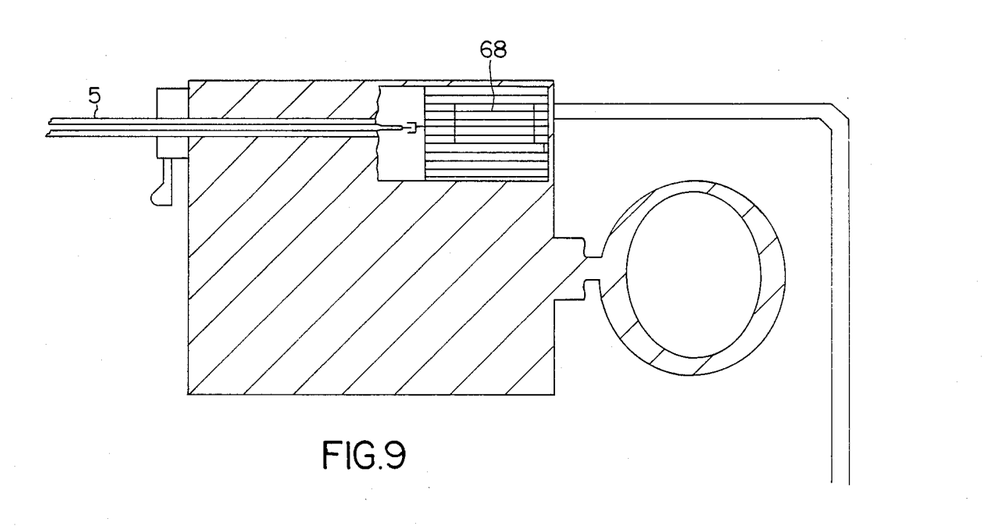
FIG. 9 is a diagrammatic representation and a longitudinal sectional view of an endoscope according to the invention with an embodiment of the arrangement of the driving motor.

FIG. 9 in principle shows the endoscope according to the parent patent, in which case, however, in longitudinal direction of the shaft 5, a motor 68 is mounted directly at this shaft 5 so that the motor shaft extends directly as an extension of the shaft 5 and a direct driving of the instrument by the motor is achieved without any inserting of gears or of power transmitting means.

Figure 10:
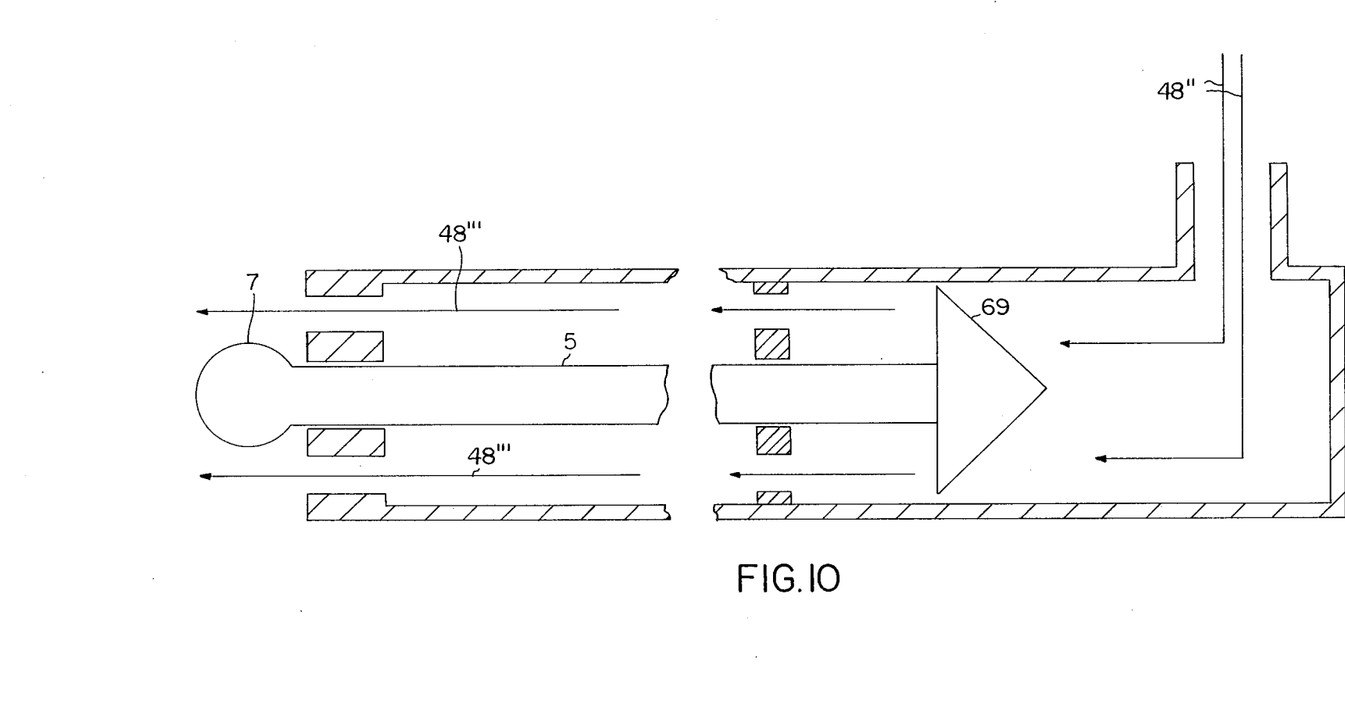
FIG. 10 is a diagrammatic representation and a longitudinal sectional view of an endoscope according to the invention with a turbine drive of the instrument.

FIG. 10 is a diagrammatic representation of a turbine drive 69 that is disposed on the shaft 5 carrying the instrument 7. According to this embodiment, the flow of the flushing liquid that in this case has the number 48" is preferably first used for driving the turbine 69 in order to then, according to the Arrows 48", continue to flow to the operating area of the instrument 7. Instead of the turbine drive by means of the flushing liquid, a compressed-air drive may also be provided. In that case, a corresponding air discharge must, however, be provided.

All shown and described characteristics as well as their appropriate combinations are significant with respect to the invention.

We claim:

1. An endoscope having a front or tip end and a rear end, and comprising a tubular housing, a lens system with a light guide extending longitudinally in said housing and having its viewing aperture at the rear end of the endoscope, a continuously driven shaft also extending longitudinally in said housing in parallel relationship to said light guide and comprising at its front end, protruding in operation from the tip of the endoscope a rotating working head, and at least one flushing duct, and means for introducing flushing liquid into said flushing duct,
wherein there are provided means for applying to said shaft independent axial and rotary movements, and
wherein said working head is a cutting instrument having a plurality of cutting blades with cutting edges.

2. An endoscope as claimed in claim 1, wherein said cutting blades are crescent shaped and wherein said plurality of cutting blades lie on a generally cylindrical surface.

3. An endoscope as claimed in claim 2, wherein the cutting edges of said blades extend at an angle to the axis of rotation of said driven shaft.

4. An endoscope as claimed in claim 1, wherein the rotating working head is in the form of a tube which is closed at one end.

5. An endoscope as claimed in claim 4, wherein the tube has a wavy cutting edge.

6. An endoscope as claimed in claim 4, wherein the endoscope also comprises a tubular element of a diameter only slightly larger than that of said rotating working head, and wherein said tubular element and said working head are arranged for longitudinal movement relatively to each other so that during the working stroke, as the working head is rearwardly withdrawn, the cutting edge of said working head slides into said tubular element in closely fitting relationship.

7. An endoscope as claimed in claim 6, wherein said counterbearing, in turn, is pot-shaped and forms together with said working head a hollow space for the collection of removed tissue.

8. An endoscope as claimed in claim 1, wherein the rotating working head is in the form of a tube which is open at both ends and has a cutting edge at each end.

9. An endoscope as claimed in claim 1, wherein the rotating working head is in the form of a truncated cone having a cutting edge.

10. An endoscope as claimed in claim 1, wherein the endoscope also comprises a turbine for driving said shaft.

11. An endoscope as claimed in claim 10, wherein said turbine is disposed in said tubular housing so that the turbine is driven by the flushing liquid.

12. An endoscope as claimed in claim 11, wherein said turbine is disposed on, and adjacent to the rear end of, said shaft within said at least one flushing duct so that the flushing liquid upon passing through the turbine is conducted to the area of the rotating working head.

13. An endoscope as claimed in claim 1, wherein the endoscope has a plurality of flushing ducts, one of said ducts connecting the flushing liquid introduced through said introducing means to the operating area of the working head and another of said flushing ducts transporting the flushing liquid returning from said area.

14. An endoscope as claimed in claim 13, wherein in said tubular housing an inner tube is formed surrounding said driven shaft and said light guide, and wherein an outer flushing duct is formed between said inner tube and said tubular housing, and an inner annular flushing duct inside said inner tube.

15. An endoscope as claimed in claim 14, wherein lateral openings are provided in the annular housing near the front end of said housing to establish communication between the outer annular flushing duct and the space outside of the tubular housing.

16. An endoscope as claimed in claim 15, wherein the outer flushing duct is connected to said introducing means to transport the introduced liquid to the area of said working head by way of said lateral openings, and the inner flushing duct is connected to discharge means to discharge the liquid returned from the area of the working head.

17. An endoscope as claimed in claim 14, wherein the inner flushing duct is connected to said introducing means to transport the introduced liquid to the area of the working head and the outer flushing duct is connected to discharge means to discharge the liquid returned from said area by way of said lateral openings.

18. An endoscope as claimed in claim 13, wherein said means for introducing and discharging the flushing liquid are provided with throttling devices, for the feeding and removal, respectively, of said flushing liquid.

19. An endoscope as claimed in claim 1, wherein means are provided for electrically heating the working head.

20. An endoscope as claimed in claim 19, wherein the working head is made of metallic material for enabling said head to be heated by electric energy caused to impinge thereon from the outside, whereas the tubular housing and the driven shaft are made of plastic material which is not being heated by said electric energy.

21. An endoscope as claimed in claim 1, wherein an electric motor driving said shaft is mounted in said endoscope coaxially with said shaft, and is directly coupled to said shaft.

* * * * *

UNITED STATES PATENT AND TRADEMARK OFFICE
CERTIFICATE OF CORRECTION

PATENT NO. : 4,950,278

DATED : Aug. 21, 1990

INVENTOR(S) : SACHSE et al.

It is certified that error appears in the above-identified patent and that said Letters Patent is hereby corrected as shown below: Title page:

Col. 2 "4,455,509 5/1989" should be -- 4,445,509 5/1984 --

Col. 1, line 8 "1986" should be -- 1988 --

" . 2, " 6 "than" should be -- then --

" . 3, " 62 after "be" insert -- a --

" . 4, " 42 "of" first occurrence, should be -- or --

Signed and Sealed this

Twenty-sixth Day of November, 1991

Attest:

HARRY F. MANBECK, JR.

Attesting Officer

Commissioner of Patents and Trademarks